(12) United States Patent
Kopparapu (10) Patent No.: US 11,534,103 B2
(45) Date of Patent: Dec. 27, 2022

(54) SYSTEM AND METHOD FOR MRI IMAGE SYNTHESIS FOR THE DIAGNOSIS OF PARKINSON'S DISEASE USING DEEP LEARNING

(71) Applicant: Neeyanth Kopparapu, Herndon, VA (US)

(72) Inventor: Neeyanth Kopparapu, Herndon, VA (US)

( * ) Notice: Subject to any disclaimer, the term of this patent is extended or adjusted under 35 U.S.C. 154(b) by 441 days.

(21) Appl. No.: 16/750,314

(22) Filed: Jan. 23, 2020

(65) Prior Publication Data

US 2020/0237284 A1    Jul. 30, 2020

Related U.S. Application Data

(60) Provisional application No. 62/796,128, filed on Jan. 24, 2019.

(51) Int. Cl.

| | |
|---|---|
| *G06K 9/00* | (2022.01) |
| *A61B 5/00* | (2006.01) |
| *G16H 30/40* | (2018.01) |
| *G06T 7/00* | (2017.01) |
| *G06N 3/08* | (2006.01) |
| *G06N 3/04* | (2006.01) |
| *G06N 20/10* | (2019.01) |

(Continued)

(52) U.S. Cl.
CPC .......... *A61B 5/4082* (2013.01); *C12Q 1/6883* (2013.01); *G06N 3/0454* (2013.01); *G06N 3/088* (2013.01); *G06N 20/10* (2019.01); *G06N 20/20* (2019.01); *G06T 7/0012* (2013.01); *G16H 30/40* (2018.01); *G06T 2207/10088* (2013.01); *G06T 2207/20081* (2013.01); *G06T 2207/20084* (2013.01)

(58) Field of Classification Search
CPC ...... G06N 20/10; G06N 20/20; G06N 3/0454; G06N 3/0472; G06N 3/088; G06N 5/003; G06N 7/005; G06T 2207/30016; G06T 7/0012; G06T 2207/10088; G06T 2207/10104; G06T 2207/20081; G06T 2207/20084; G06T 2207/10096; G06T 2207/10108; G06T 2207/20128; G06T 2207/20132; G06T 3/40; G06T 7/11; G06T 7/174; G06T 7/194
See application file for complete search history.

(56) References Cited

PUBLICATIONS

Tagaris, "Assessment of Parkinson's Disease Based on Deep Neural Networks," Sep. 2018 (Year: 2018).*

(Continued)

*Primary Examiner* — Alex Kok S Liew
(74) *Attorney, Agent, or Firm* — Hunton Andrews Kurth LLP (57) ABSTRACT

Systems and methods for diagnosis of Parkinson's disease (PD) using machine learning are disclosed. In one embodiment, a method may include receiving, on at least one processor, data, comprising one or more Magnetic Resonance Images (MRI) from a human subject; preprocessing the one or more MRIs; applying one or more Convolutional Neural Networks (CNNs) to perform image analysis of the one or more MRIs; applying one or more Generative Adversarial Networks (GANs) to augment a dataset of artificial scans for classification training; outputting, using the at least one processor, a classification based on the one or more MRI images a diagnosis of the subject for PD.

20 Claims, 10 Drawing Sheets

(51) Int. Cl.
    C12Q 1/6883      (2018.01)
    G06N 20/20       (2019.01)

(56) References Cited

PUBLICATIONS

Frid-Adar, "GAN-based synthetic medical image augmentation for increased CNN performance in liver lesion classification," Jan. 2018, Elsevier (Year: 2018).*
Shah, "Detection of Parkinson Disease in Brain MRI using Convolutional Neural Network," Sep. 2018, Proceedings of the 24th International Conference on Automation & Computing, Newcastle University (Year: 2018).*
Warwick R. Adams, "High-accuracy detection of early Parkinson's Disease using mul-tiple characteristics of finger movement while typing". In: PLOS ONE 12.11 (Nov. 2017), pp. 1-20. DOI: 10.1371/journal.pone.01.88226. URL: https://doi.org/10.1371/journal.pone.0188226.
Antreas Antoniou et al., "Data Augmentation Generative Adversarial Networks". In: abs/1803.01229 (2018). URL: https://arxiv.org/abs/1803.01229.
Huiling Chen, "An efficient diagnosis system for detection of Parkinson's disease using fuzzy k-nearest neighbor approach". In: Expert Systems with Applications (Jan. 2013).
Mayo Clinic, Parkinson's Disease Diagnosis and Treatment. URL: https://www.mayoclinic.org/diseases-conditions/parkinsons-disease/diagnosis-treatment/drc-20376062.
Mayo Clinic, Parkinson's Disease Symptoms and Causes. URL: https://www.mayoclinic.org/diseases-conditions/parkinsons-disease/symptoms-causes/syc-20376055.
Emily Downward, Diagnosis & Early Symptoms & Early Diagnosis. 2017. URL: https://parkinsonsdisease.net/diagnosis/early-symptoms-signs/.
Tom Fawcett, "An introduction to ROC analysis". In: Pattern Recognition Letters (2006).
Suhua Feng et al., "Determining DNA methylation profiles using sequencing." In: Methods Molecular Biology 733 (2011), pp. 223-238. DOI: 10.1007/978-1-61779-089-8 16. URL: https://link.springer.com/protocol/10.1007/978-1-61779-089-816.
Y. Feng et al., "Epigenetic mechanisms in Parkinson's disease". In: J. Neurol. Sci. 349.1-2 (Feb. 2015), pp. 3-9 (abstract only).
Maayan Frid-Adar et al. "GAN-based Synthetic Medical Image Augmentation for increased CNN Performance in Liver Lesion Classification". In: CoRR abs/1803.01229 (2018). arXiv: 1803.01229. URL: http://arxiv.org/abs/1803.01229.
David Gil and Magnus Johnsson. "Diagnosing Parkinson by using artificial neural networks and support vector machines", eng. In: Global Journal of Computer Science and Technology. Global Journal of Computer Science and Technology 9.4 (2009), pp. 63-71. ISSN: 0975-4172.
Ian J. Goodfellow et al., "Generative Adversarial Networks". In: abs/1406.2661 (2014). URL: https://arxiv.org/abs/1406.2661.
Griewing et al., "The importance of MRI (magnetic reso-nance imaging) for the diagnosis of brainstem infarction". In: Bildgebung Imaging 59 (Jul. 1992), pp. 94-97 (abstract).
X. Hao et al, "DNA methylation markers for diagnosis and prognosis of common cancers". In: Proc. Natl. Acad. Sci. U.S.A. 114.28 (Jul. 2017), pp. 7414-7419.
Xiaoke Hao et al. "DNA methylation markers for diagnosis and prognosis of common can-cers". In: Proceedings of the National Academy of Sciences 114.28 (2017), pp. 7414-7419. ISSN: 0027-8424. DOI: 10.1073/pnas.1703577114.eprint: http://www.pnas.org/content/114/28/7414.full.pdf. URL: http://www.pnas.org/content/114/28/7414.
Kaiming He et al. "Deep Residual Learning for Image Recognition". In: CoRR (2015). eprint: 1512.03385. URL: http://arxiv.org/abs/1512.03385.
A J Hughes et al. "Accuracy of clinical diagnosis of idiopathic Parkinson's disease: a clinico-pathological study of 100 cases." In: Journal of Neurology, Neurosurgery & Psychiatry 55.3 (1992), pp. 181-184. DOI: http://doi.org/10.1136/innp.55.3.181.
Andrew J. Hughes et al. "What features improve the accuracy of clinical diagnosis in Parkin-son's disease". In: Neurology 42.6 (1992), pp. 1142-1142., eprint: http://n.neurology,org/content/42/6/1142.full.pdf. URL: http://n.neurology.org/content/42/6/1142 (abstract only).
Takako Jones et al. "Identifying diagnostic DNA methylation profiles for facioscapulo-humeral muscular dystrophy in blood and saliva using bisulfite sequencing". In: Clin Epige-netics 6.1 (2014), p. 23. DOI: 10.1186/1868-7083-6-23. URL: https://clinicalepigeneticsjournal.biomedcentral.com/articles/10.1186/1868-7083-6-23.
G. Jurman et al, "A Comparison of MCC and CEN Error Measures in Multi-Class Prediction". In: PLoS ONE 7.8 (2012).
A. Keshavarzian et al. "Colonic bacterial composition in Parkinson's disease". In: Mov. Disord. 30.10 (Sep. 2015), pp. 1351-1360.
M. Kim et al. "DNA methylation as a biomarker for cardiovascular disease risk". In: PLoS ONE 5.3 (Mar. 2010), e9692.
Quoc V. Le, Navdeep Jaitly, and Geoffrey E. Hinton. "A Simple Way to Initialize Recurrent Networks of Rectified Linear Units". In: CoRR abs/1504.00941 (2015). arXiv: 1504.00941. URL: http://arxiv.org/abs/1504.00941.
Fredrik Lundh. Python Imaging Library (PIL). 2018. URL: http://www.pythonware.com/products/pil/.
Martin Abadi et al. TensorFlow: Large-Scale Machine Learning on Heterogeneous Systems. Software available from tensorflow.org. 2015. URL: http://tensorflow.org/.
MathWorks. Introduction to Deep Learning—what are Convolutional Neural Networks. 2017. URL: https://www.mathworks.com/videos/introduction-to-deep-learning-what-are-convolutional-neural-networks-1489512765771.html.
M. A. Nalls et al. "Baseline genetic associations in the Parkinson's Progression Markers Initiative (PPMI)". In: Mov. Disord. 31.1 (Jan. 2016), pp. 79-85.
L. Navarro-Sanchez et al. "Epigenetic Study in Parkinson's Disease: A Pilot Analysis of DNA Methylation in Candidate Genes in Brain". In: Cells 7.10 (Sep. 2018).
Dimitrios Siganos Christos Stergiou. Neural Networks. Imperial College London, 1996. URL: https://www.doc.ic.ac.uk/~nd/surprise 96/journal/vol4/cs11/report.html.
Clayton R. Pereira et al. "A Step Towards the Automated Diagnosis of Parkinson's Disease: Analyzing Handwriting Movements". In: 2015 IEEE 28th International Symposium on Computer-Based Medical Systems (2015), pp. 171-176.
CR Pereira et al. "A new computer vision-based approach to aid the diagnosis of Parkinson's disease." In: Comput Methods Programs Biomed 136 (2016), pp. 79-88. DOI: http://doi.org/10.1016/j.cmpb.2016.08.005.
G Rizzo et al. "Accuracy of clinical diagnosis of Parkinson disease: A systematic review and meta-analysis". In: Neurology 86.6 (2016), pp. 566-576. DOI: http://doi.org/10.1212/WNL.0000000000002350.
Karen Simonyan and Andrew Zisserman. "Very Deep Convolutional Networks for Large-Scale Image Recognition". In: CoRR abs/1409.1556 (2014). arXiv: 1409.1556. URL: http://arxiv.org/abs/1409.1556.
Jasper Snoek, Hugo Larochelle, and Ryan Adams. "Practical Bayesian Optimization of Machine Learning Algorithms". In: Advances in Neural Information Processing Systems (2012). eprint: 1206.2944. URL: https://arxiv.org/abs/1206.2944.
University of Southern California. Parkinson's Progression Markers Initiative. URL: https://ida.loni.usc.edu/login.jsp?project=PPMI.
M. Stone. "Cross-Validatory Choice and Assessment of Statistical Predictions". In: Journal of the Royal Statistical Society. Series B (Methodological) 36.2 (1974), pp. 111-147. ISSN: 00359246.
Christian Szegedy et al. "Going Deeper with Convolutions". In: CoRR abs/1409.4842 (2014). arXiv: 1409.4842. URL: http://arxiv.org/abs/1409.4842.
C. Tanner and S. Goldman. "Epidemiology of Parkinsons disease". In: Neurologic Clinics 14 (1996), pp. 317-335. DOI: https://dx.doi.org/10.1007/s00702-017-1686-y (abstract only).
Keras Team. Keras. 2018. URL: https://github.com/keras-team/keras.

(56) References Cited

PUBLICATIONS

B. Thomas and M. F. Beal. "Parkinson's disease". In: Hum. Mol. Genet. 16 Spec No. 2 (Oct. 2007), R183-194.
Yu-Xiong Wang et al. "Low-Shot Learning from Imaginary Data". In: CoRR abs/1801.05401 (2018). arXiv: 1801.05401. URL: http://arxiv.org/abs/1801.05401.
K.E. Watkins et al. "Structural Asymmetries in the Human Brain: a Voxel-based Statistical Analysis of 142 MRI Scans". In: Cerebral Cortex 11.9 (2001), pp. 868-877. DOI: 10.1093/cercor/11.9.868. eprint: /oup/backfile/content public/journal/cercor/11/9/10.1093 cercor 11.9.868/1/1100868.pdf. URL: http://dx.doi.org/10.1093/cercor/11.9.868.
WebMD. Parkinson's Causes. URL: https://www.webmd.com/parkinsons-disease/guide/parkinsons-causes#1.
WebMD. Parkinson's Later Diagnosis. URL: https://www.webmd.com/parkinsons-disease/news/20101004/parkinsons-later-diagnosis-earlier-death#1.
Tao Wu and Mark Hallett. "A functional MRI study of automatic movements in patients with Parkinson's disease". In: Brain 128.10 (2005), pp. 2250-2259. DOI: 10.1093/brain/awh569. eprint: /oup/backfile/content public/journal/brain/128/10/10.1093/brain/awh569/2/awh569. pdf. URL: http://dx.doi.org/10.1093/brain/awh569.

\* cited by examiner

| ConvNet Configuration | | | | | |
|---|---|---|---|---|---|
| A | A-LRN | B | C | D | E |
| 11 weight layers | 11 weight layers | 13 weight layers | 16 weight layers | 16 weight layers | 19 weight layers |
| input (224 × 224 RGB image) | | | | | |
| conv3-64 | conv3-64 LRN | conv3-64 conv3-64 | conv3-64 conv3-64 | conv3-64 conv3-64 | conv3-64 conv3-64 |
| maxpool | | | | | |
| conv3-128 | conv3-128 | conv3-128 conv3-128 | conv3-128 conv3-128 | conv3-128 conv3-128 | conv3-128 conv3-128 |
| maxpool | | | | | |
| conv3-256 conv3-256 | conv3-256 conv3-256 | conv3-256 conv3-256 | conv3-256 conv3-256 conv1-256 | conv3-256 conv3-256 conv3-256 | conv3-256 conv3-256 conv3-256 conv3-256 |
| maxpool | | | | | |
| conv3-512 conv3-512 | conv3-512 conv3-512 | conv3-512 conv3-512 | conv3-512 conv3-512 conv1-512 | conv3-512 conv3-512 conv3-512 | conv3-512 conv3-512 conv3-512 conv3-512 |
| maxpool | | | | | |
| conv3-512 conv3-512 | conv3-512 conv3-512 | conv3-512 conv3-512 | conv3-512 conv3-512 conv1-512 | conv3-512 conv3-512 conv3-512 | conv3-512 conv3-512 conv3-512 conv3-512 |
| maxpool | | | | | |
| FC-4096 | | | | | |
| FC-4096 | | | | | |
| FC-1000 | | | | | |
| soft-max | | | | | |

| Convolutional Network Configuration |
|---|
| Convolutional 3D (512) x 3 Layers |
| Max-Pooling 3D (4x4x4) |
| Convolutional 3D (128) x 4 Layers |
| Max-Pooling 3D (4x4x4) |
| Convolutional 3D (16) x 4 Layers |
| Max-Pooling 3D (2x2x2) |
| Convolutional 3D (8) x 2 Layers |
| Global Averaging 3D (2x2x2) |
| FC - 512 |
| FC - 16 |
| Softmax |

SYSTEM AND METHOD FOR MRI IMAGE SYNTHESIS FOR THE DIAGNOSIS OF PARKINSON'S DISEASE USING DEEP LEARNING

CROSS REFERENCE TO RELATED APPLICATIONS

This application claims priority to U.S. Provisional Application No. 62/796,128, filed on Jan. 24, 2019, the contents of which are incorporated herein in its entirety.

FIELD OF THE INVENTION

The present disclosure relates generally to a method of treating a patient that has Parkinson's disease (PD). Exemplary embodiments include a tool for the automatic augmentation of 3D Magnetic Resonance Imaging datasets using Machine Learning (specifically Generative Adversarial Networks).

BACKGROUND OF THE INVENTION

Parkinson's disease (PD) is the second most prevalent neurodegernative disease, affecting approximately 1% of the population above the age of 65. While the disease itself is not fatal, complications related to PD are rated as the 14th largest cause of death in the United States by the Center of Disease Control and Prevention. PD affects movement, originally with small tremors, slowness of movement, and shortness of breath, but symptoms worsen as the condition progresses while untreated. Although the exact cause of PD has not been determined, PD is known to kill cells in the substanitia nigra, the area of the brain responsible for the production of dopamine, a neurotransmitter responsible for the control of movement. The loss of dopamine, an early sign of Parkinson's, leads to symptoms including bradykinesia, the slowness of movement. Therefore, it is important for patient's future for them to have a quick and accurate diagnosis.

Due to the lack of a specific diagnosis pipeline for PD, the accuracy of diagnosis has not increased despite the advancements in the fields of medicine, technology, and bioinformatics. The accuracy of diagnosis reported in 1992 from 100 various studies was 82%, and the accuracy in 2014 was 83.9%. These methods include analyzing years of neurological data to determine if the patient has developed the symptoms of Parkinson's, including limb rigidity and tremors, both of which are common side effects of a number of other diseases. Although numerous computational vision attempts at diagnosing PD have emerged, including automatically regressing neurological data and classifying patient micrography, efforts haven't reached classification metrics that compare to manual efforts, with accuracies near 67%.

These and other deficiencies exist.

SUMMARY OF THE INVENTION

Exemplary embodiments include a tool for the automatic augmentation of certain data sets, such as 3D Magnetic Resonance Images ("MRI"), motor assessment, and methylation, datasets using Machine Learning (specifically Generative Adversarial Networks or GANs). Data demonstrates that this tool was able to increase the diagnosis of Parkinson's Disease from 80.6% in early stages to 96.6%. Generative networks have been used to create data for other uses, but in exemplary embodiments GANs are used to generate whole 3D MRI images. Generative networks have been used to create slices or patches (2D) but not whole images as done by exemplary embodiments. This creation of the whole image has led to a significantly larger increase in accuracy of diagnosis according to exemplary embodiments. Additionally, exemplary embodiments adapting the GANs for modularity since the majority of machine learning models can only work for images or data with a specific shape, for example images that are exactly 256×512, but the model according to exemplary embodiments is able to work with any shape of the MRI scan as long as it is a whole 3D scan.

An embodiment includes a system to carry out the method according to exemplary embodiments. The system may include various components and different computer systems, including components that are physically separated and remote from one another. A first computer may be used to access a remotely located server on which the method according to exemplary embodiments is executed. The first computer may access the server through an interface, such as a web-based interface. The output of the method may be provided through the web-based interface. The method may be carried out over a computer based network, such as the Internet.

This and other embodiments and advantages will become apparent from the following detailed description, taken in conjunction with the accompanying drawings, illustrating by way of example, the principles of the various embodiments.

BRIEF DESCRIPTION OF THE DRAWINGS

For a more complete understanding of the preferred embodiments, the objectives and advantages thereof, various figures are included herein. These figures are exemplary.

DETAILED DESCRIPTION OF PREFERRED EMBODIMENTS

The following description provides different configurations and features according to exemplary embodiments. While certain nomenclature and types of applications and software are described, other names, and applications and software usage are possible. The nomenclature provided is done so by way of a non-limiting example. Further, while particular embodiments are described, it should be appreciated that the features and functions of each embodiment may be combined in any combination as is within the capability of one of ordinary skill in the art. The figures provide additional exemplary details of the various embodiments. It should also be appreciated that the following exemplary embodiments are provided as non-limiting examples.

The embodiments described herein are exemplary because there are a variety of ways to carry out methods according to the present disclosure. The methods and systems depicted and described can be executed or otherwise performed by one or a combination of various systems and modules. Each block shown in the embodiment represents one or more processes, decisions, methods or subroutines carried out in the exemplary method, and these processes, decisions, methods or subroutines are not necessarily carried out in the specific order outlined in the methods, nor is each of them required.

Exemplary embodiments include a tool which may be referred to as PDGAN. This name is meant to be non-limiting. PDGAN is a tool to aid pathologists and neurologists in the diagnosis of PD. PDGAN may use a series of neural networks to classify MRI Images. PDGAN employs GANs to synthetically generate medical images which is used to augment classification efforts. The pair of Convolutional Neural Networks (CNNs) exhibited an testing accuracy of 91.4% without the augment of new data, and combined the total accuracy was 96.6%, a 16% increase compared to traditional methods at a fraction of the cost and time. PDGAN demonstrates the feasibility of utilizing GANs to generate unseen data for the improvement of classification accuracy in the medical setting. PDGAN has also found genes whose change in expression occur commonly in patients with Parkinson's Disease. Exemplary embodiments of PDGAN are unique in the ability to diagnose PD with an augmented, generated dataset as described herein. With around 12,000 MRI machines in the US, the applicability of the system and method according to exemplary embodiments is widespread.

The current procedure for testing for PD is as follows: (1) a physical exam is conducted, (2) further lab tests are conducted (Blood Work, MRI, Brain Ultrasound), (3) manual analysis of past neurological history, (4) determine if symptoms are present. These non-deterministic tests often take weeks and produce unreliable results. It is also very difficult to predict symptoms until they are already present, and the longer PD goes undiagnosed in a patient, the harder it is for any treatment to be effective.

With the rise of automated prediction algorithms paired with the generation of massive amounts of data, the automatic diagnosis of Parkinson's disease has not caught up to traditional means. This is commonly attributed to the lack of useful data, as most computational systems require a tremendous amount of medical data that isn't readily available as gathering the data can be expensive.

Many previous studies attribute their difficulties to two main problems. First, there is a lack of useable data. Complex regression and deep learning models that include millions of parameters require a hundreds or thousands of data points to learn from, and many available datasets contain anywhere from 50 to 200 images, not nearly enough for capable models to converge. Second, studies determined the hardest diagnosis class for PD is the patients right after showing signs of symptoms. At this stage, symptoms have not fully present, so it is nearly impossible for neurologists or automatic tools to detect the presence of PD.

Exemplary embodiments present an automated approach to aid the diagnosis of PD through patient MRI scans. MRI scans have historically been used to determine alterations in the Central Nervous System (CNS), some of which might be indicative of PD. MRI scans have been shown to be more effective than other imaging processes in displaying these changes, and most diagnosis efforts from scientists include an MRI scan of the brain. The approach uses a system of Fully Convolutional Networks (FCNs) and Convolutional Neural Networks (CNNs) to perform image analysis tasks. It also utilizes Generative Adversarial Networks (GANs) to augment the current dataset with more artificial scans that were used in the classification training.

Dataset Description The data used for the system came from the University of Southern California's Laboratory of Neurological Imaging (LONI) (*Parkinson's Progression Markers Initiative*. URL: https://ida.loni.usc.edu/login.jsp?project=PPMI). The Parkinson's Progression Markers Initiative under LONI's Image Data Archive contains MRI scans, genetic data, medical history, and motor assessments from over 1400 Parkinson's and Control patients. The Image Archive contains 921 Control MRIs and 2633 PD MRIs viewed in the Axial form.

MRI is an imaging procedure that uses magnets and radio waves to capture detailed images of the brain. Although there are many types of MRI scans, including functional MRIs (fMRI), cardiac MRIs, Magnetic resonance angiography (MRA), and Magnetic resonance venography (MRV), the most common MRI is a anatomical scan of the brain. This anatomical scan displays the shape, volume, and developmental changes in the brain as a three-dimensional image.

Figure 1:
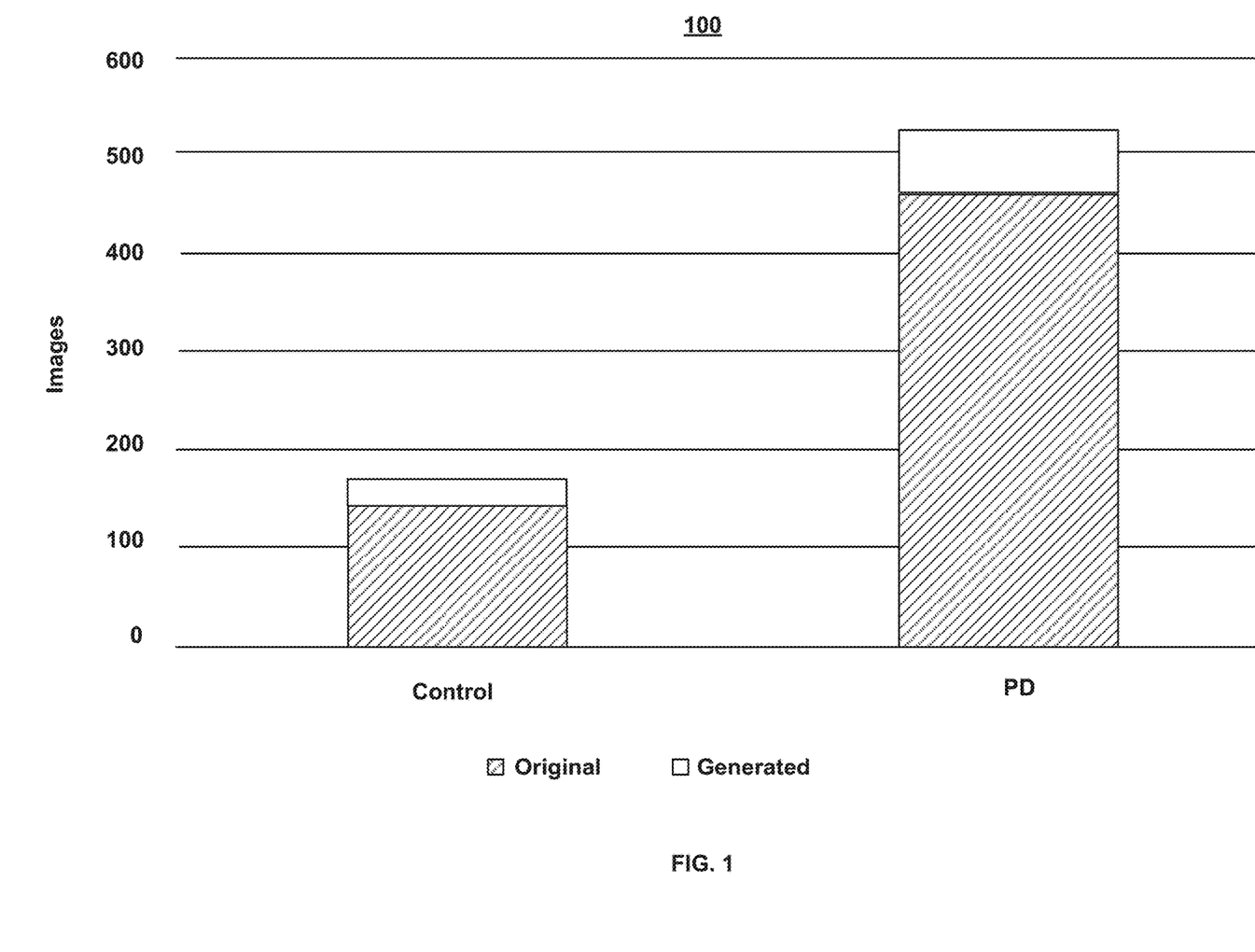
FIG. 1 illustrates a chart displaying sizes of generated and original datasets according to exemplary embodiments.

The anatomical MRIs obtained from the data archive came in 43 different sizes, ranging from 1024×1024×256 to 32×24×32. Due to the large variance in sizes, the data actually used was one that had a high volume of images, but also had a representative split compared to the total dataset. The chosen size was 256×240×176, as it had a total of 612 images, 146 from the Control group, and 466 from the PD group, representative of the approximate 1:3 split in data described herein. The 86 generated images had 23 MRIs of the control group and 63 MRIs of the PD group, keeping consistent with the same ratio as the previous data as shown in FIG. 1 in the graph 100.

Additionally, as part of the PPMI dataset, 524 patients (389 with Parkinson's Disease and 135 without) had reported Methylation beta values for over 850000 different CpG islands located in the human genome, as measured by the Infinium MethylationEPIC array.

Software and Hardware The software platform used for the creation of this project was Python. Python was used due to its modularity and compatibility with numerous standard machine learning, plotting, and artificial intelligence frameworks. To perform standard image preprocessing and analysis tasks, the OpenCV and PIL (Python Imaging Library) libraries were used.

Both Tensorflow and Keras were used as deep learning frameworks. Keras was used due to its code readability and modularity, and Tensorflow was used for its extensive online documentation, as well as its use for machine learning, mathematical computation, and deep learning. Artificial Neural Networks (ANNs) were used to perform the classification task. ANNs have grown in popularity for outperforming humans in various tasks, including computer analysis tasks.

Figure 2:
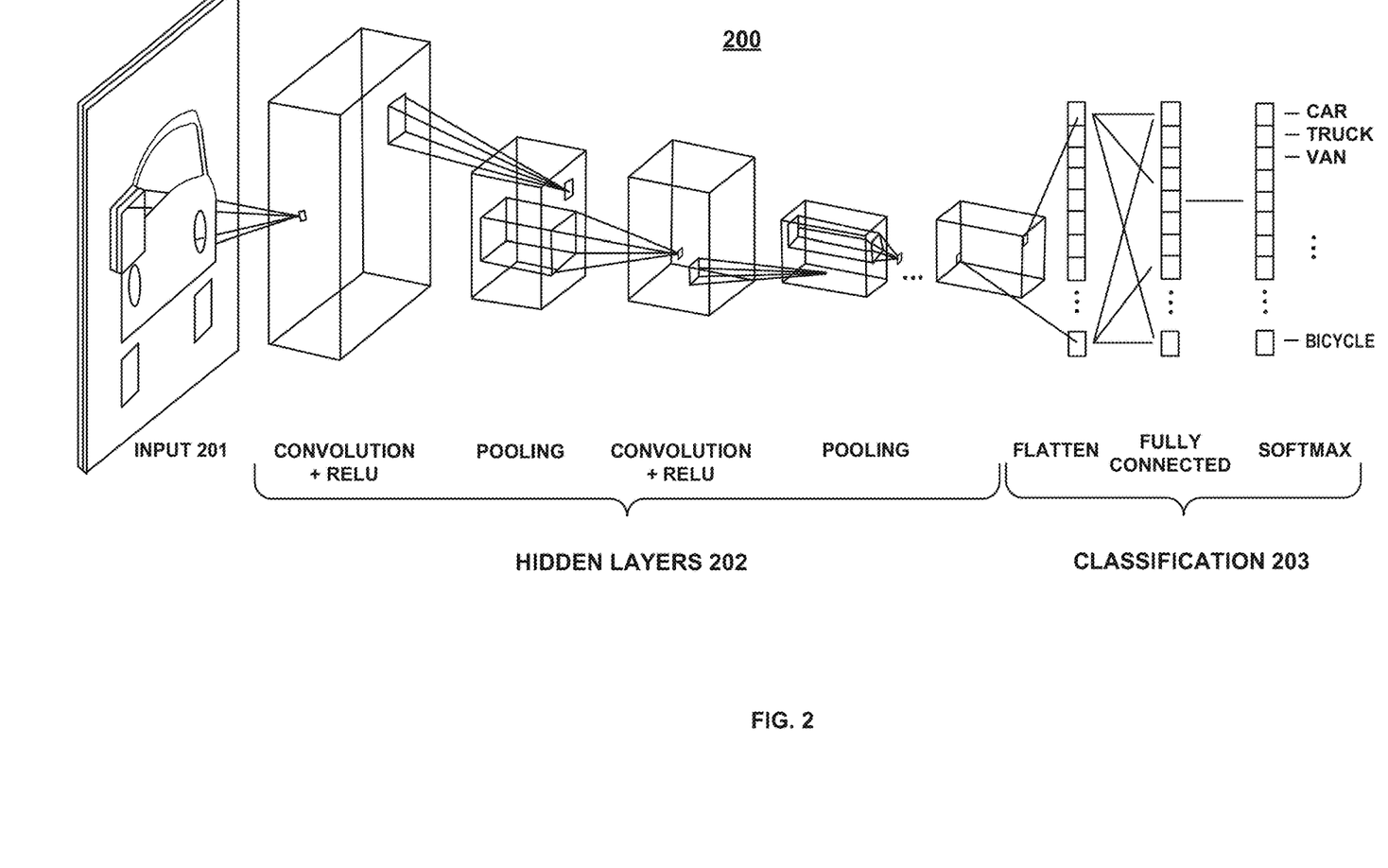
FIG. 2 illustrates an exemplary Fully Convolutional Neural Network (CNN) that has convolution layers.

Convolutional Neural Networks (CNNs) and Generative Adversarial Networks (GANs) were utilized. CNNs are a flavor of ANNs that specialize in image processing. FIG. 2 shows the basis of what CNN 200 does. For example, CNN 200 processes an input 201 with several different hidden layers 202 to produce an output classification 203. Each hidden layer detects a different feature of the input 201.

Figure 3:
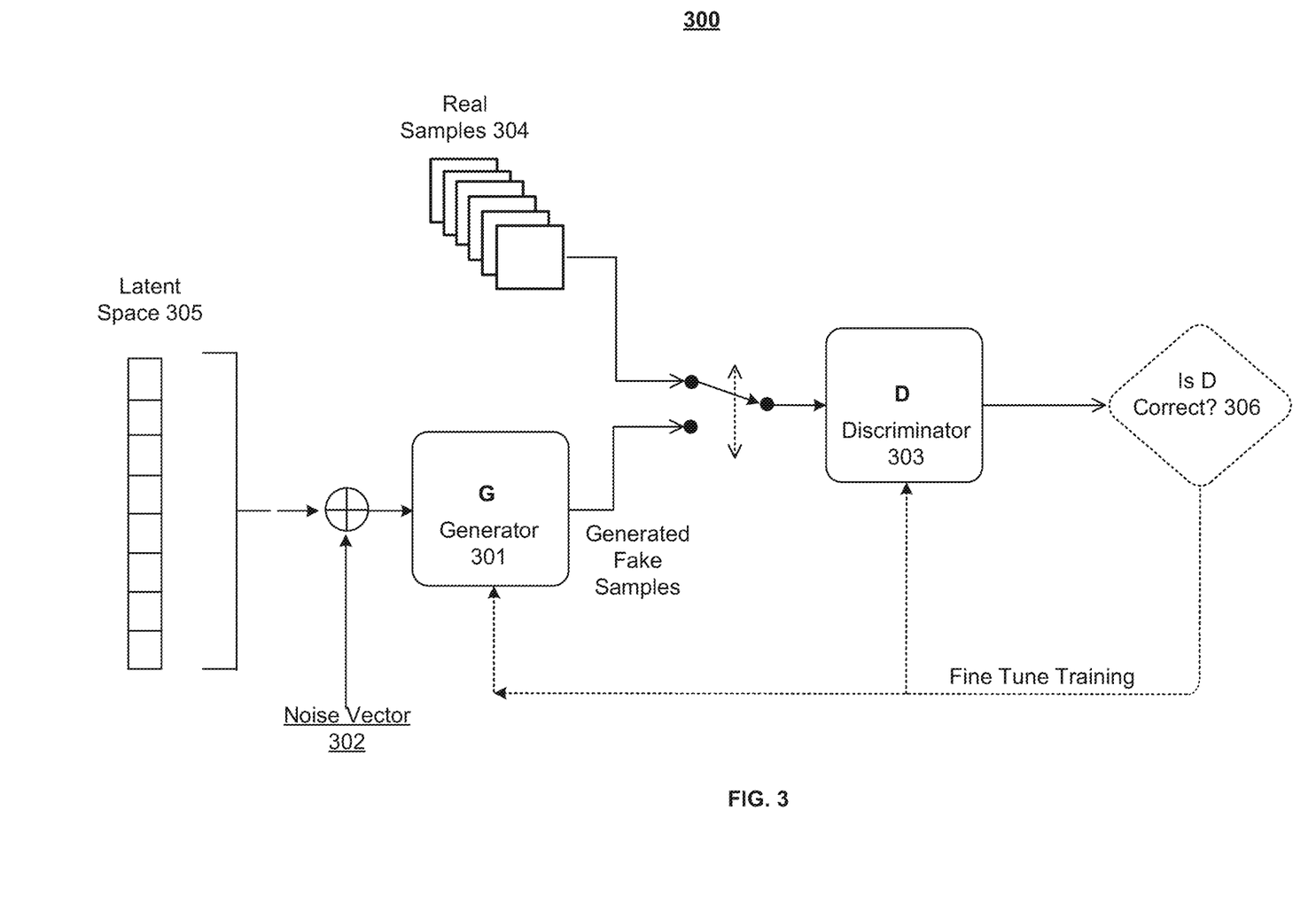
FIG. 3 illustrates an exemplary Generative Adversarial Network (GAN) data flow (Stack Exchange).

GANs, in the class of unsupervised machine learning, are a version of an adversarial network which works to generate images similar to the samples given using a noise vector. As shown in FIG. 3, the GAN 300 comprises a Generator 301 that takes a noise vector 302 which it uses, in addition to a sample from a training set, e.g. latent space 305, to create a randomly altered image to test the Discriminator 303. The Discriminator 303 is tasked to determine if an inputted image is a real sample 304 or a fake sample output by the generator 301. If the Discriminator 303 correctly determines an input image is a Real Sample 304 (306), the Generator 301 updates its parameters to create better fake samples to fool the Discriminator 303 via Fine Tune Training. If the Discriminator's prediction is incorrect at 306, i.e. it is fooled to believe the Generator's input image is a Real Sample 304, the Discriminator 303 tries to learn from its mistake to avoid similar mistakes in the future via Fine Tune Training. The adversarial network's goals are to make it harder for each other, and in turn improve. GANs are trained over thousands of epochs to converge, but these epochs take less time compared to traditional training epochs.

To complete the task, a Tesla K80 GPU was used, which included 11.2 GB of GPU memory, and 4992 CUDA cores. A p2.xlarge AWS EC2 instance was used with an Ubuntu backend and 100 GB extra SWAP space to store data during program calls.

Approach—Preprocessing Minimal preprocessing steps were taken. First, the images were normalized. The images were not subjected to standard augmentation procedures including cyclic pooling and tilting because hemispherical asymmetries in MRI images can reveal important features of the brain anatomy. The dimensions of the image array after preprocessing were 256×240×176.

Figure 4:
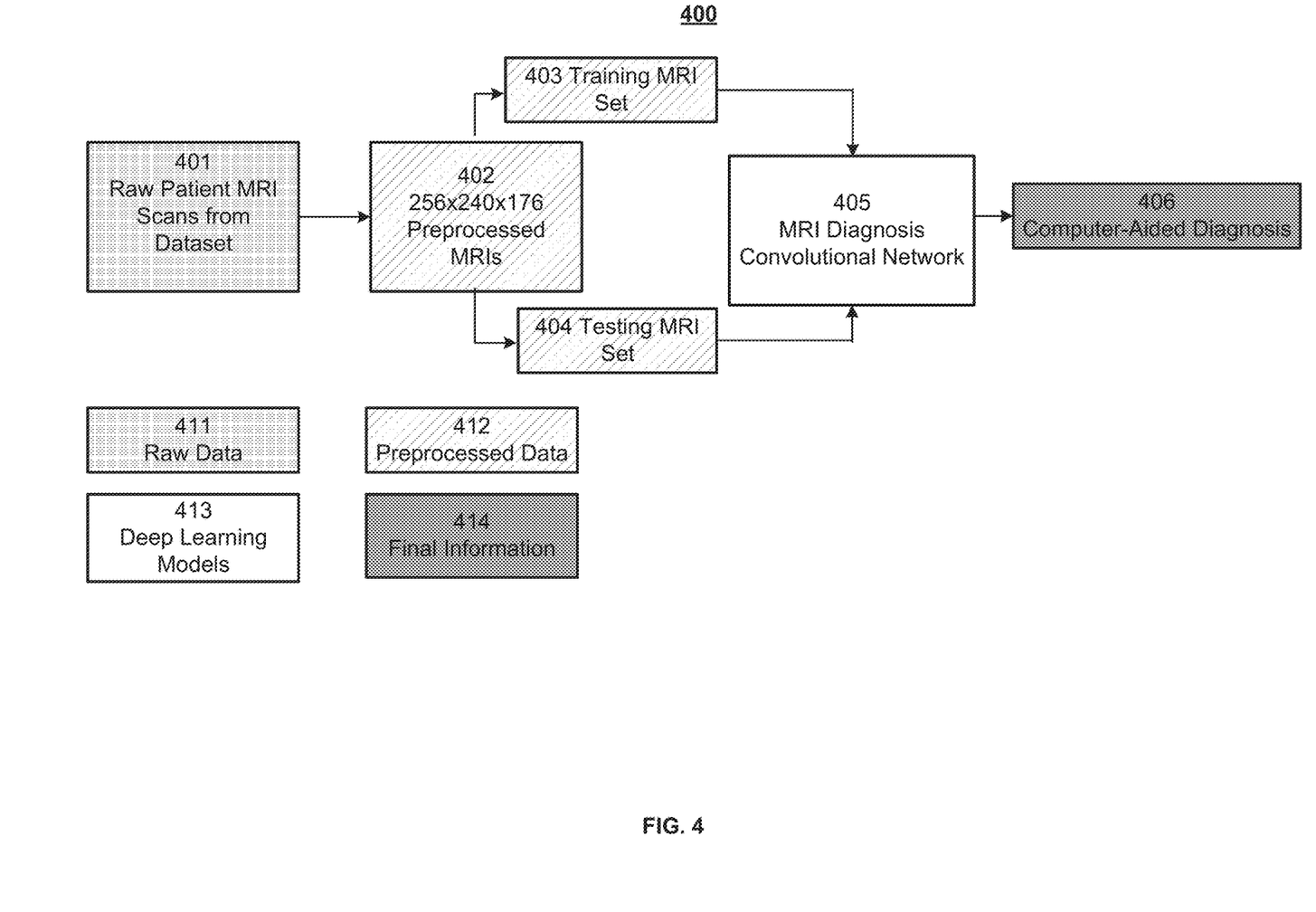
FIG. 4 illustrates the flow of data and processing according to exemplary embodiments.

Approach—First Iteration The first iteration of the system includes preprocessing steps and the image classification neural network, trained only on the images in LONI's PPMI database. FIG. 4 shows the flow of data in the system 400. For example, in 401 raw data, e.g. raw patient MRI scans from the data set are obtained. In step 402, the images are normalized without being subjected to standard augmentation procedures, and the image array after preprocessing is, for example. 256×240×176. A Training MRI Set 403, and a Testing MRI Set 404 are generated thereafter. The Training MRI Set 403, and Testing MRI Set 404 are thereafter applied to deep learning models, e.g. traditional CNNs as described more fully below, in step 405 for MRI Diagnosis. Finally, in step 406 computer-aided diagnosis is applied to the results of the MRI Diagnosis.

FIG. 4 contains rectangular graphics having different shading patterns to express different states of the information contained in the flow chart. Raw Data 411 is shown in rectangles having a grid shading; Preprocessed Data 412 is shown in a green color rectangles having upward diagonal shading; rectangles having no shading are used to denote where Deep Learning Models 413 are applied to the data; and gray is rectangles having a solid shading are used to show data as Final Information 414 as ready to be presented.

Figure 5:
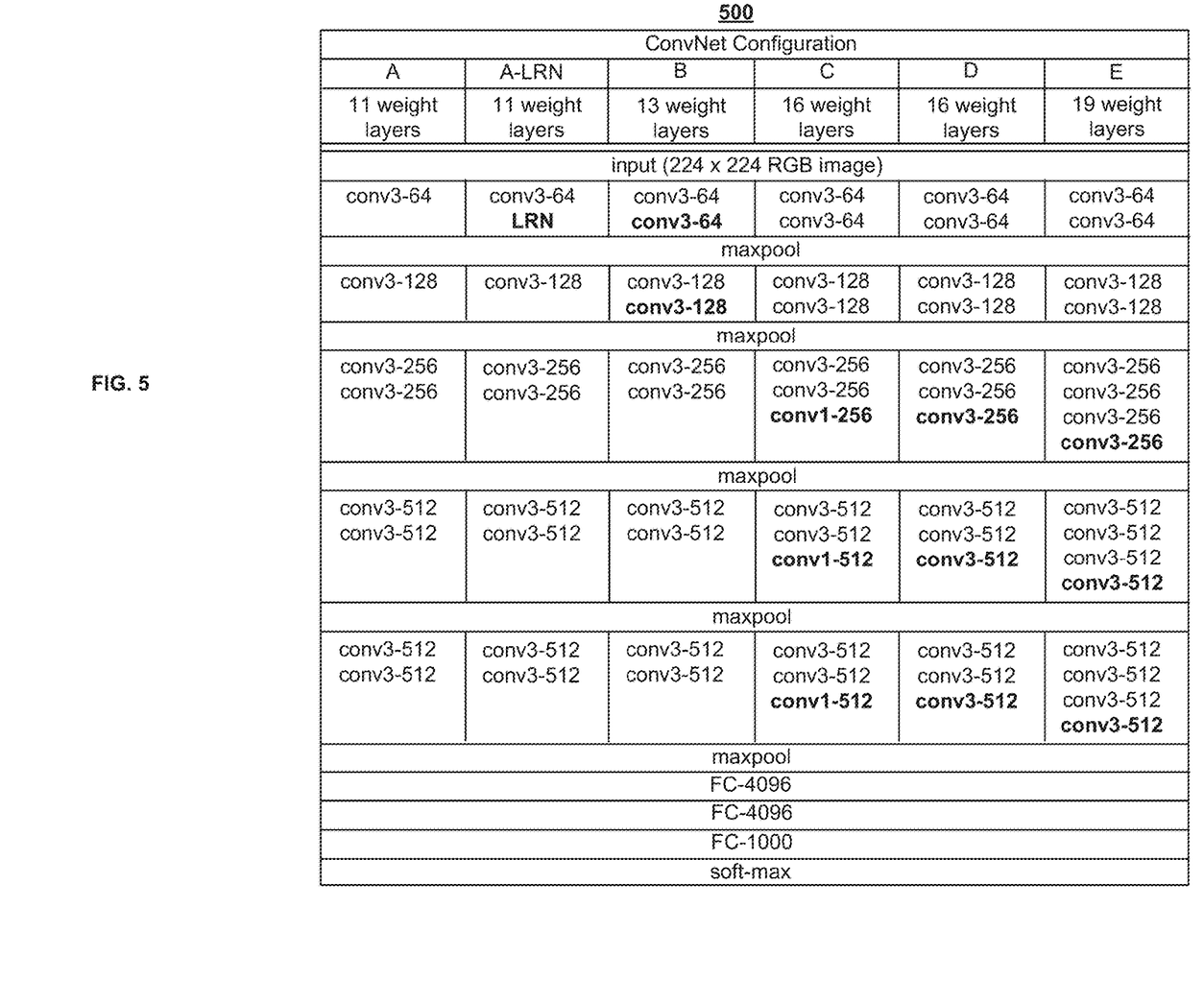
FIG. 5 illustrates an exemplary VGG system architecture

There were various models used, in an attempt to maximize accuracy. First, traditional CNNs, including the VGG-19, GoogLeNet, and Resnet-50, were used due to their high accuracy in standard benchmarks like ImageNet (Karen Simonyan and Andrew Zisserman. "Very Deep Convolutional Networks for Large-Scale Image Recognition". In: *CoRR* abs/1409.1556 (2014). arXiv: 1409.1556. URL: http://arxiv.org/abs/1409.1556; Christian Szegedy et al. "Going Deeper with Convolutions". In: *CoRR* abs/1409.4842 (2014). arXiv: 1409.4842. URL: http://arxiv.org/abs/1409.4842; Kaiming He et al. "Deep Residual Learning for Image Recognition". In: *CoRR* (2015). eprint: 1512.03385. URL: http://arxiv.org/abs/1512.03385). The VGG model is described in FIG. 5 in the table 500, where "E" is the VGG-19 model. Because MRIs are three dimensional, the CNNs were repurposed for 3D classification.

To further improve the accuracy, the Spearmint package was used (see, e.g., Jasper Snoek, Hugo Larochelle, and Ryan Adams. "Practical Bayesian Optimization of Machine Learning Algorithms". In: *Advances in Neural Information Processing Systems* (2012). eprint: 1206.2944. URL: https://arxiv.org/abs/1206.2944). Spearmint, a Bayseian optimization package which changes hyperparameters to minimize loss, was used on the VGG-19 model which had the highest accuracy before using the package. With 5 variables to change the different size of the filter layers, the model's accuracy was increased slightly to 91.4%. Spearmint was not allowed to fully complete its optimization due to time constraints, as each trial would take upwards of 6 hours with early stopping. Thus, only 18 spearmint programs were run.

To improve the accuracy of exemplary embodiments, some problems were highlighted.

1. The size of the dataset is small—with over 400 million parameters, only a few hundred images is not enough to make the model converge.

2. With deep networks like the vanilla GoogLeNet, the vanishing gradient problem only allowed small changes to be made progressively, with large changes not having much of an impact on the early layers.

In exemplary embodiments, steps were taken to combat these problems, all of which were reflected in the second interaction of the model.

Approach—Motivation Wang et al. described one of the first methods of augmenting a dataset during low-shot learning (Yu-Xiong Wang et al. "Low-Shot Learning from Imaginary Data". In: *CoRR* abs/1801.05401 (2018). arXiv: 1801.05401. URL: http://arxiv.org/abs/1801.05401). The hallucinator, G, described is able to take an input (x,y), with a noise vector z and output a "hallucinated" input (x', y) that would then be used to augment the original training data. The hallucinator used was a multilayer perceptron. An objective of exemplary embodiments was. to similarly augment the training set with new MRI scans. However, exemplary embodiments used a three layer MLP, which would not be able to make the complex transformations necessary to generate the 3-dimensional scans.

Kingma and Welling described the first methods of generation using encoders (Diederik Kingma and Max Welling. "Auto-Encoding Variational Bayes". In: abs/1312.6114 (2014). URL: https://arxiv.org/abs/1312.6114), but like Wang et al., the networks described were used for simple image tasks with small data sets and small dimensional images. Goodfellow et al.'s work with GANs and the image generation process created not only a generator (similar to the hallucinator previously), but also a discriminator—serving as the adversarial network in the pair (Ian J. Goodfellow et al. "Generative Adversarial Networks". In: abs/1406.2661 (2014). URL: https://arxiv.org/abs/1406.2661). The GAN would fix the problem of a small dataset.

According to exemplary embodiments, auxiliary classifiers were used to solve the problem of the vanishing gradient.

Figure 6:
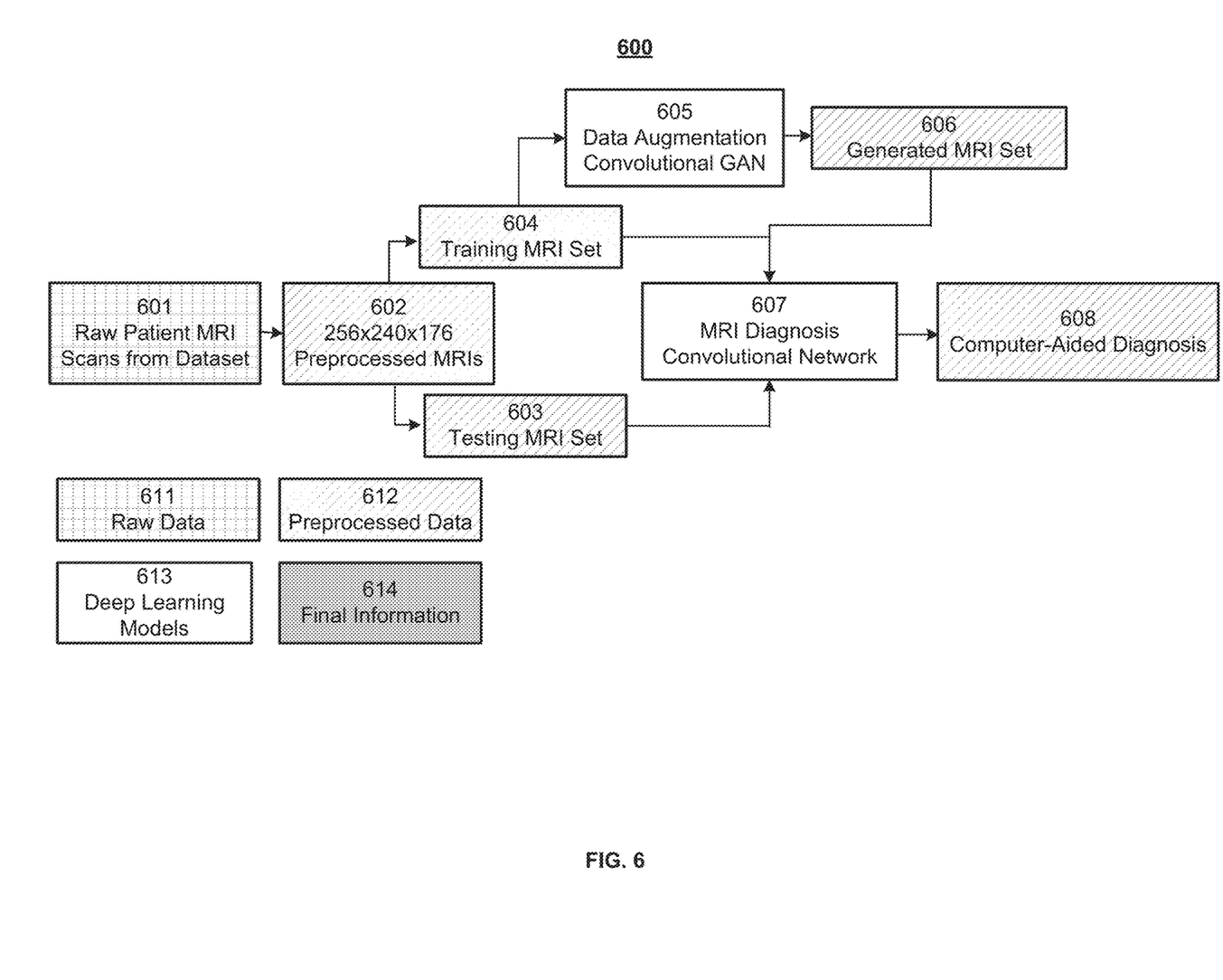
FIG. 6 illustrates a flow of data and processing according to exemplary embodiments.

Approach—Second Iteration The second iteration of the system includes two network models—one for image classification and the final diagnosis, and one for artificial image synthesis for data augmentation—shown in FIG. 6 in the method 600. The images are from a shared dataset, but the images used to train the GAN as well as the ones generated by the GAN were only used in the training set for the classifier. This meant that only real images not seen by either the GAN or classifier in training made up the evaluation (test) set. For example, in 601 raw data, e.g. raw patient MRI scans from the data set are obtained. In step 602, the images are normalized and the image array after preprocessing is, for example, 256×240×176. A Training MRI Set 604, and a Testing MRI Set 603 are generated thereafter. Data Augmentation, as described more fully above, is applied to the Training MRI Set 604 in step 605 via a convolutional GAN, to generate a new MRI Set 606. The MRI Set 606 and the Testing MRI Set 603 are thereafter applied to deep learning models, e.g. traditional CNNs, in step 607 for MRI Diagnosis. Finally, in step 608 computer-aided diagnosis is applied to the results of the MRI Diagnosis.

FIG. 6 contains rectangular graphics having different shading patterns to express different states of the information contained in the flow chart. Raw Data 611 is shown in a blue color rectangles having a grid shading; Preprocessed Data 612 is shown in rectangles having upward diagonal shading; rectangles having no shading are used to denote where Deep Learning Models 613 are applied to the data; and rectangles having a solid shading are used to show data as Final Information 614 as ready to be presented.

Figure 7:
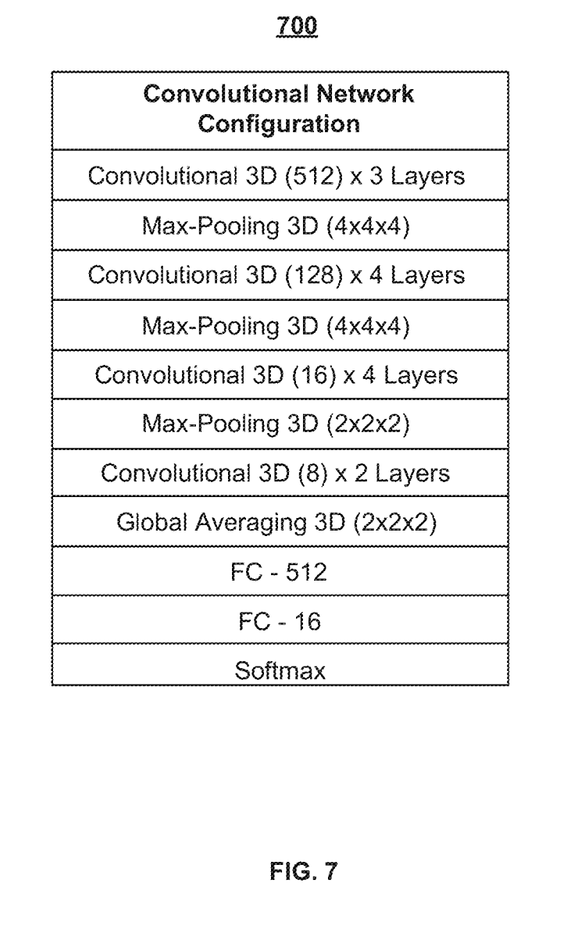
FIG. 7 illustrates model configuration characteristics for an exemplary PDGAN model.

The same architectures from the first iteration (VGG, GoogLeNet, and Resnet) were trained again to determine the effects of the addition to the dataset. Additionally, one other set of networks was used, including a feature extractor appended to a classification network. Auxiliary classifiers were added throughout the VGG, GoogLeNet, Resnet, and new models. The generator network's weights were initialized as block diagonal identity matrices. The architecture of the new model is described in FIG. 7 at 700.

According to exemplary embodiments, the same optimizations made after model creation for the first iteration were applied to the second, including using Spearmint. To validate the results, the k-fold cross-validation in M. Stone, "Cross-Validatory Choice and Assessment of Statistical Predictions" from the Journal of the Royal Statistical Society. Series B (Methodological) 36.2 (1974), pp. 111-147 (ISSN: 00359246.)

Approach—Genetic Markers The analysis of the methylation values mirrored analysis done by other studies involving DNA methylation, using a non-spatial predictor to determine if the patient had Parkinson's Disease. To do this, an ensemble classifier was used including a Random Forest Classifier, Multi-Layer Perceptron, and Support Vector Machine.

Each of the classifiers were trained individually to value entropy over impurity, both of which are options used for training classification trees like the Random Forest Classifier. The models underwent the same training and k-fold cross-validation the image analysis models went through over the 524 data points in the PPMI dataset. Because there was no possibility for external verification for the data, no synthetic data was generated for this task.

Because PCA was used for dimensionality reduction, the problem of establishing which CpG islands (features) were more important was not straightforward. Suppose the initial data with 864067 parameters was labeled as a 524×864067 matrix A. The PCA matrix, P, of size 864067×32, reduced the input space to 524×32 A' where A'=AP. The feature importance generated by the Random Forest Classifier was a 1×32 matrix F, so to recreate the importance for all the original parameters, F needs to be combined with the transpose of A, so F'=FAT where F' is the actual feature importance for all original features.

Results according to exemplary embodiments are described below.

First Iteration The following table indicates accuracy, sensitivity, and specificity of the three classification algorithms after the 15 training epochs.

TABLE 1 accuracy, sensitivity, and specificity of the three models.

| Model | Accuracy | Sensitivity | Specificity |
|---|---|---|---|
| VGG-19 | 90.20% | 93.10% | 81.08% |
| GoogLeNet | 84.97% | 86.21% | 81.08% |
| Resnet-50 | 88.89% | 92.24% | 78.38% |

$$\text{Sensitivity} = \frac{TP}{TP + FN} \quad \text{Specificity} = \frac{TN}{TN + FP}$$

Figure 8:
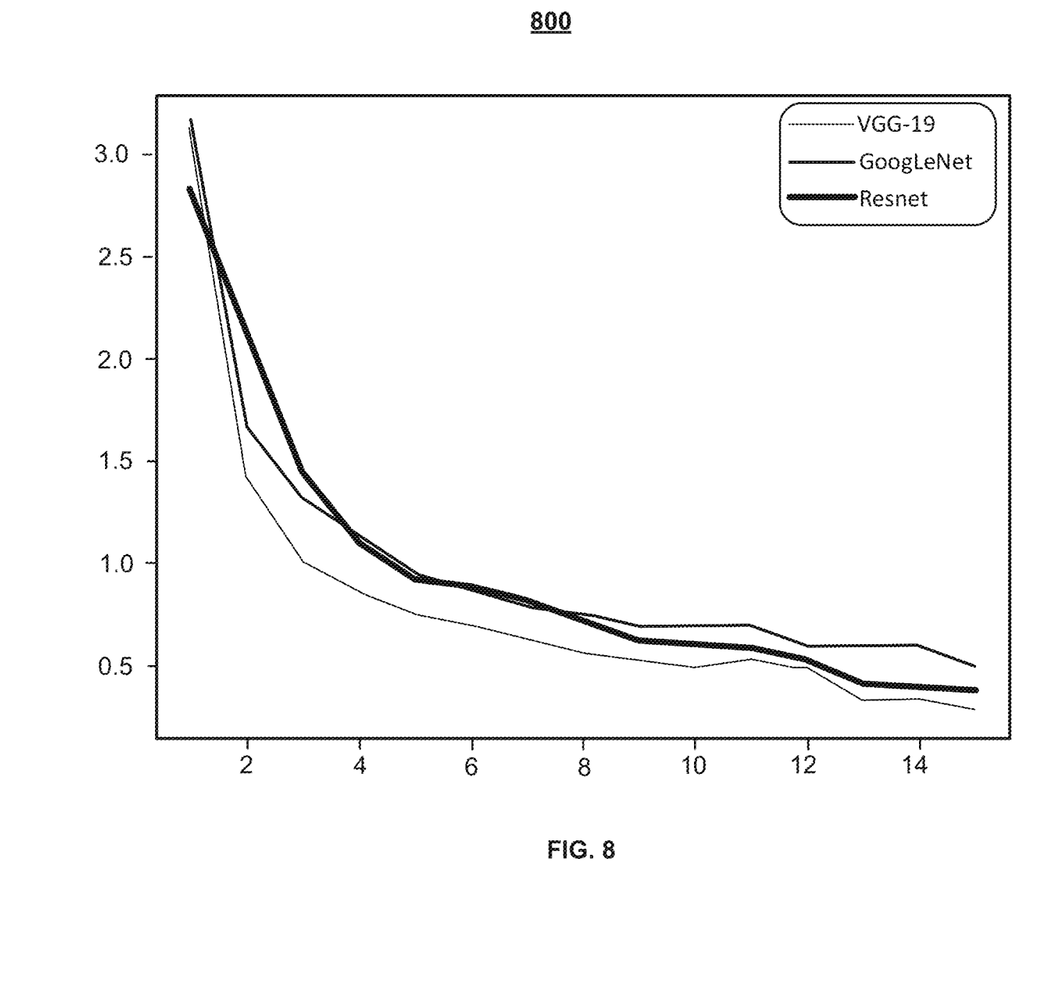
FIG. 8 illustrates validation loss graphs according to exemplary embodiments.

The number of epochs, 15, was chosen as a part of the Early Stopping callback in Keras (Keras Team. Keras. 2018. URL: https://github.com/keras-team/keras), which continues the training of the algorithm until the validation loss experiences multiple epochs of no decrease. The graphs of loss are depicted in FIG. 8 in the graph 800 that shows validation loss graphs of the three models depicted in Table 1 through the 15 epochs.

The model's weights were fine-tuned to attain improved performance on the validation set, and had minimal overfitting due to many empirically tested methods, including adding dropout, regularization, and patience.

Figure 9:
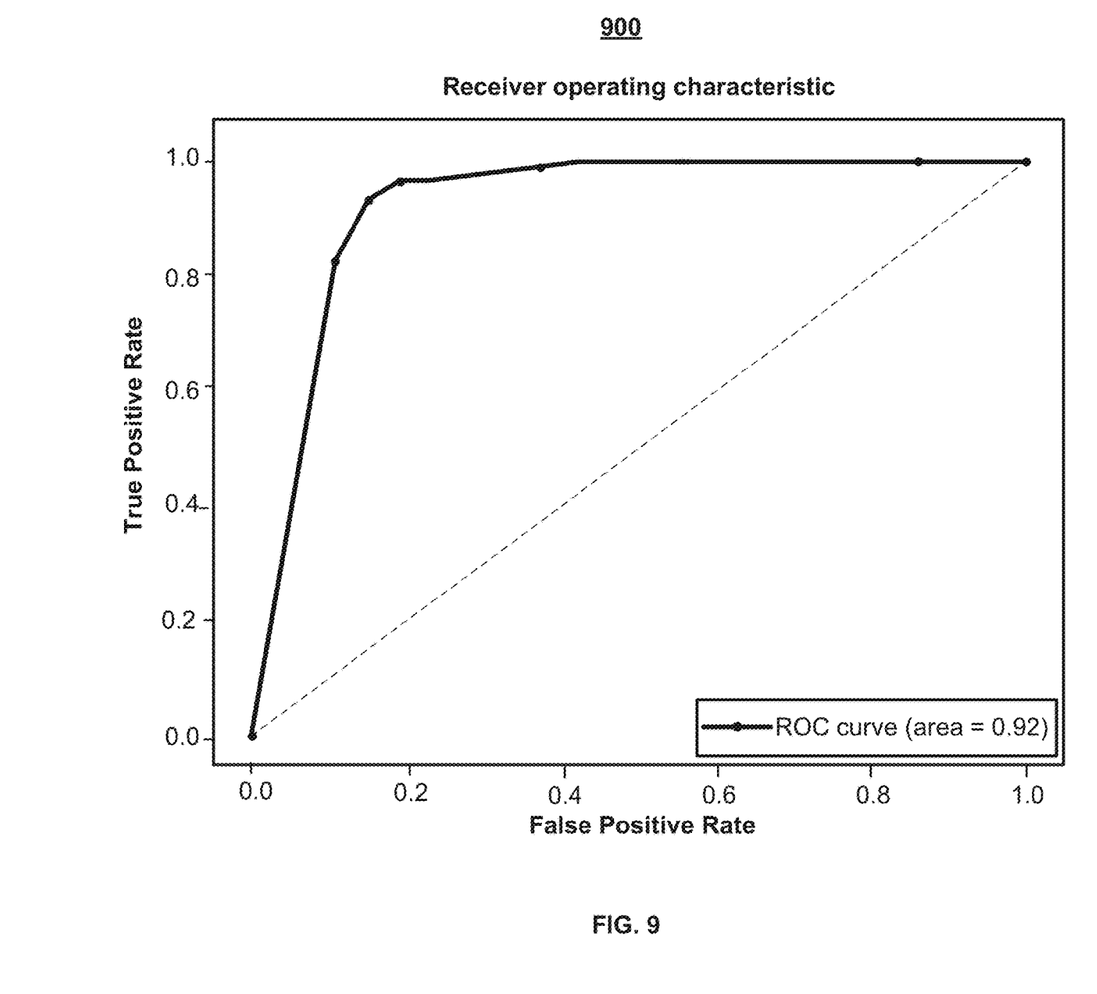
FIG. 9 illustrates a receiving operating characteristic curve for an exemplary VGG model.

After using the spearmint package, the accuracy of the VGG model was increased to 91.4%. The ROC curve for the finalized model is given in FIG. 9 at 900.

Second Iteration With the addition of the GAN, the three models performed significantly better. In addition, the new model created surpassed the accuracy of the previous and new models. Table 2 gives the accuracy, sensitivity, and specificity of the new models.

TABLE 2 accuracy, sensitivity, and specificity of the four new models.

| Model | Accuracy | Sensitivity | Specificity |
|---|---|---|---|
| VGG-19 | 94.12% | 94.83% | 91.89% |
| GoogLeNet | 91.50% | 92.24% | 89.19% |
| Resnet-50 | 89.54% | 87.93% | 94.59% |
| PDGAN | 96.62% | 97.41% | 94.59% |

Figure 10:
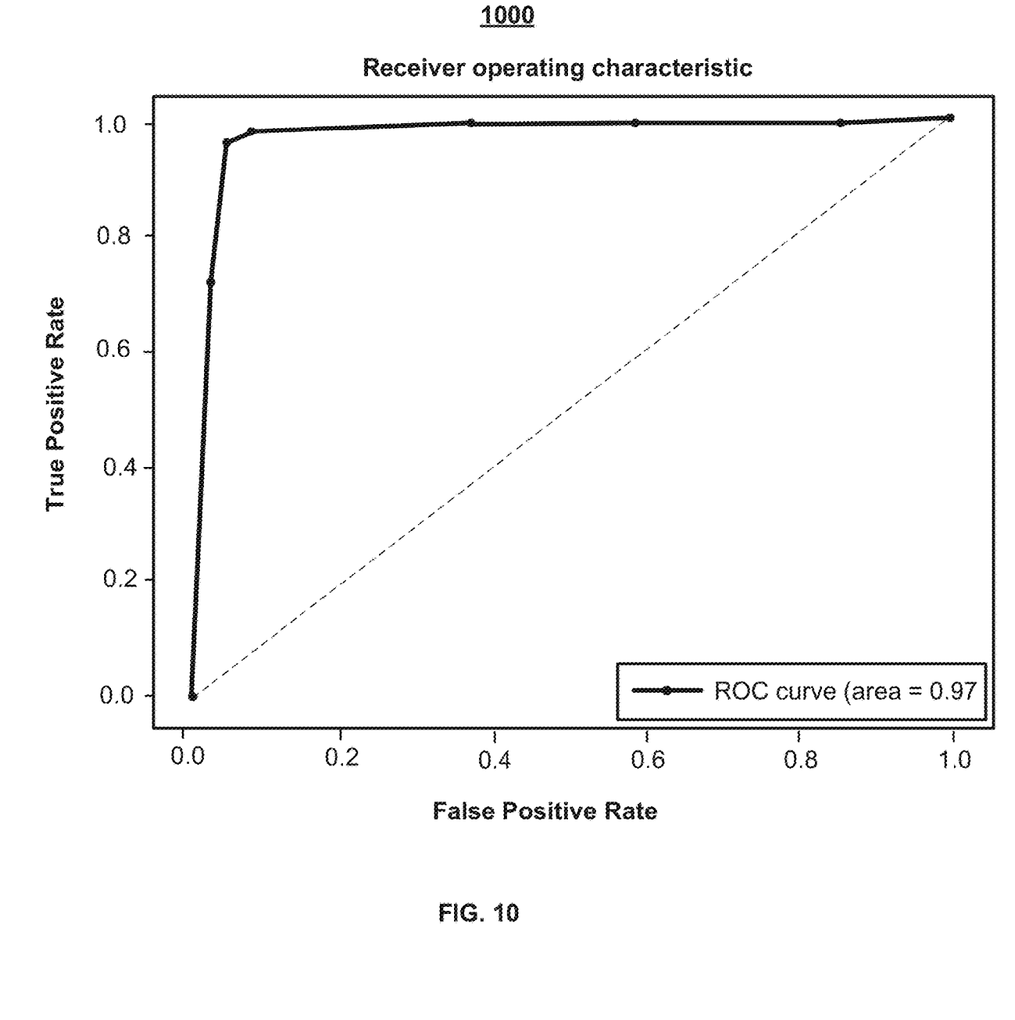
FIG. 10 illustrates a receiving operating characteristic curve for an exemplary PDGAN model.

To determine the effects of only the addition of the new data, the same number of epochs was used for each system, namely 15. However, it was evident the model was still able to learn more, as the loss formed a monotonic decreasing sequence. Looking at the ROC curve 1000 in FIG. 10, as it is a common evaluation metric among medical devices, it is evident that PDGAN's performance is better than all the first iteration models due to the increase in dataset.

Genetic Markers The ensemble classification efforts yielded an accuracy of 85%, lower than the MRI-based classification attempts but still better than current clinical efforts. Additionally, the Random Forest Classifier was able to rank every parameter based off the importance it made to the classification process. Among the top five included islands related to the PRKN gene and SV IL gene. The PRKN gene, which codes for the Parkinson protein is known to be related to Parkinson's Disease. The SV IL gene, which codes for the Supervillin gene, is not known to be immediately related to the disease.

The primary objective of exemplary embodiments is to improve on the current diagnosis system for PD and increase the chance for early diagnosis among patients. As many patients get MRI scans done as a preliminary test during PD screening, analyzing MRI scans for early signs of Parkinson's Disease was ideal because of the MRI's ability to analyze the anatomy of the brain with high precision. Computationally generating an alternative diagnosis gives neurologists the power to access second opinions in a time and money efficient manner. This is crucial for the well-being of patients, as treatment plans become less accessible for patients with Parkinson's in later stages.

Table 3 illustrates several related studies, and their difference to the PDGAN's methodology. (Huiling Chen. "An efficient diagnosis system for detection of Parkinson's disease using fuzzy k-nearest neighbor approach". In: *Expert Systems with Applications* (January 2013); Clayton R. Pereira et al. "A Step Towards the Automated Diagnosis of Parkinson's Disease: Analyzing Handwriting Movements". In: 2015 *IEEE 28th International Symposium on Computer-Based Medical Systems* (2015), pp. 171-176; Maayan Frid-Adar et al. "GAN-based Synthetic Medical Image Augmentation for increased CNN Performance in Liver Lesion Classification". In: *CoRR* abs/1803.01229 (2018). arXiv: 1803.01229. URL: http://arxiv.org/abs/1803.01229; David Gil and Magnus Johnsson. "Diagnosing Parkinson by using artificial neural networks and support vector machines". eng. In: Global Journal of Computer Science and Technology 9.4 (2009), pp. 63-71. ISSN: 0975-4172; Warwick R. Adams. "High-accuracy detection of early Parkinson's Disease using multiple characteristics of finger movement while typing". In: *PLOS ONE* 12.11 (November 2017), pp. 1-20. DOI: 10.1371/journal.pone.0188226. URL: https://doi.org/10.1371/journal.pone.0188226)).

TABLE 3 information about several related studies and the difference between each of those studies and exemplary embodiments.

| Study | Description | Input Data | Methodology | Accuracy | Difference between study |
|---|---|---|---|---|---|
| Chen, 2013 | FKNN-based Diagnosis | Voice Measurements | Fuzzy K-Nearest Neighbors | 96.07% | Had thousands of sample data |
| Frid-Adar et al. | Liver Lesion Classification | Liver Lesion Images | GANs, CNNs | 88.4% | Used GANs but with a different classifier-low accuracy |
| Gil. et al. | MLP-based Diagnosis | Voice Measurements | MLP and SVM | 92.31% | Had thousands of sample data |
| Adams, 2017 | Typing based Diagnosis | Typing Movements | Various Machine Learning Models | 96.1% | Had thousands of sample data |
| Pereisa et al | Writing and Medical Exam Diagnosis | Handwriting, MedicalExam Information | Computer Vision Processing, CNNs, MLP | 67% | Low accuracy, used a combination of tests. |

Several performance metrics for all seven systems are summarized in Table 4, and demonstrate the positive effect of adding generated images to the dataset.

TABLE 4 accuracy, sensitivity, and specificity of the seven models. The bolded models indicate ones that had access to the augmented data.

| Model | Accuracy | Sensitivity | Specificity |
|---|---|---|---|
| PDGAN | 96.62% | 97.41% | 94.59% |
| VGG-19 | 94.12% | 94.83% | 91.89% |
| VGG-19 | 94.12% | 94.83% | 91.89% |
| GoogLeNet | 84.97% | 86.21% | 81.08% |
| GoogLeNet | 91.50% | 92.24% | 89.19% |
| Resnet-50 | 88.89% | 92.24% | 78.83% |
| Resnet-50 | 88.89% | 87.93% | 94.59% |

All publications, patents, and published patent applications mentioned in this specification are herein incorporated by reference, in their entirety, to the same extent as if each individual publication, patent, or published patent application was specifically and individually indicated to be incorporated by reference.

It will be readily understood by those persons skilled in the art that the various embodiments are susceptible to broad utility and application. Many embodiments and adaptations other than those herein described, as well as many variations, modifications and equivalent arrangements, will be apparent from or reasonably suggested by the various embodiments and foregoing description thereof, without departing from the substance or scope of the various embodiments.

Accordingly, while the various embodiments have been described here in detail in relation to its exemplary embodiments, it is to be understood that this disclosure is only illustrative and exemplary of the various embodiments and is made to provide an enabling disclosure of the various embodiments. Accordingly, the foregoing disclosure is not intended to be construed or to limit the various embodiments or otherwise to exclude any other such embodiments, adaptations, variations, modifications or equivalent arrangements.

What is claimed is:

1. A computer implemented method for diagnosis of Parkinson's disease (PD) comprising:
   receiving, on at least one processor, data, comprising one or more Magnetic Resonance Images (MRI) from a human subject;
   preprocessing the one or more MRIs;
   applying one or more Convolutional Neural Networks (CNNs) to perform image analysis of the one or more MRIs;
   applying one or more Generative Adversarial Networks (GANs) to augment a dataset of artificial scans for classification training;

outputting, using the at least one processor, a classification based on the one or more MRI images a diagnosis of the subject for PD; and receiving, on the at least one processor, data, comprising one or more values associated with DNA methylation from the human subject;

training at least one ensemble classifier;

applying the at least one ensemble classifier to the one or more values associated with the DNA methylation from the human subject to determine if the human subject has PD; and outputting, using the at least one processor, the determination.

2. The computer implemented method of claim 1, wherein the one or more MRIs are preprocessed without cyclic pooling and tilting.

3. The computer implemented method of claim 1, wherein dimensions of an array of the one or more MRIs after preprocessing is approximately 256×240×176 pixels.

4. The computer implemented method of claim 1, wherein the one or more CNNs used to perform the image analysis comprises of one of VGG-19, GoogLeNet, and Resnet-50.

5. The computer implemented method of claim 1, wherein the one or more CNNs used to perform the image analysis comprises VGG-19 and the Spearmint package.

6. The computer implemented method of claim 1, wherein the one or more GANs comprises applying a noise vector to a training set of the one or more MRIs.

7. The computer implemented method of claim 1, wherein the one or more CNNs comprises at least one auxiliary classifier.

8. The computer implemented method of claim 1, wherein a network weight of a generator of the one or more CNNs is initialized as at least one block diagonal identity matrix.

9. The computer implemented method of claim 1, wherein the dataset of artificial scans for classification training is different than a testing MM set used in the application of the one or more CNNs.

10. The computer implemented method of claim 1, wherein the least one ensemble classifier comprises a Random Forest Classifier, Multi-Layer Perceptron, or Support Vector Machine.

11. A computer implemented system for diagnosis of Parkinson's disease (PD) comprising:
at least one processor configured to perform the steps of:
receiving data, comprising one or more Magnetic Resonance Images (MRI) from a human subject;
preprocessing the one or more MRIs;
applying one or more Convolutional Neural Networks (CNNs) to perform image analysis of the one or more MRIs;
applying one or more Generative Adversarial Networks (GANs) to augment a dataset of artificial scans for classification training;
outputting a classification based on the one or more MRI images a diagnosis of the subject for PD; and
receiving data, comprising one or more values associated with DNA methylation from the human subject;
training at least one ensemble classifier;
applying the at least one ensemble classifier to the one or more values associated with the DNA methylation from the human subject to determine whether the human subject has PD; and
outputting the determination.

12. The computer implemented system of claim 11, wherein the one or more MRIs are preprocessed without cyclic pooling and tilting.

13. The computer implemented system of claim 11, wherein dimensions of an array of the one or more MRIs after preprocessing is approximately 256×240×176 pixels.

14. The computer implemented system of claim 11, wherein the one or more CNNs used to perform the image analysis comprises of VGG-19, GoogLeNet, or Resnet-50.

15. The computer implemented method of claim 11, wherein the one or more CNNs used to perform the image analysis comprises VGG-19 and the Spearmint package.

16. The computer implemented method of claim 11, wherein the one or more GANs comprises applying a noise vector to a training set of the one or more MRIs.

17. The computer implemented method of claim 11, wherein the one or more CNNs comprises at least one auxiliary classifier.

18. The computer implemented method of claim 11, wherein a network weight of a generator of the one or more CNNs is initialized as at least one block diagonal identity matrix.

19. The computer implemented method of claim 11, wherein the dataset of artificial scans for classification training is different than a testing MRI set used in the application of the one or more CNNs.

20. The computer implemented method of claim 11, wherein the least one ensemble classifier comprises a Random Forest Classifier, Multi-Layer Perceptron, or Support Vector Machine.

* * * * *

UNITED STATES PATENT AND TRADEMARK OFFICE
CERTIFICATE OF CORRECTION

| | |
|---|---|
| PATENT NO. | : 11,534,103 B2 |
| APPLICATION NO. | : 16/750314 |
| DATED | : December 27, 2022 |
| INVENTOR(S) | : Neeyanth Kopparapu |

It is certified that error appears in the above-identified patent and that said Letters Patent is hereby corrected as shown below:

In the Claims

In Claim 9, Column 11, Line 37, please delete "MM" and insert --MRI--.

Signed and Sealed this
Twenty-first Day of February, 2023

Katherine Kelly Vidal
*Director of the United States Patent and Trademark Office*